(12) United States Patent
Kiuchi et al.

(10) Patent No.: US 6,600,943 B1
(45) Date of Patent: Jul. 29, 2003

(54) METHOD FOR DETECTING A SPECIFIC PORTION OF ORGANISM SPECIMEN, METHOD FOR PHYSIOLOGICAL MEASUREMENT OF ORGANISM SPECIMEN, APPARATUS FOR DETECTING A SPECIFIC PORTION OF ORGANISM SPECIMEN, AND A DEVICE FOR HOLDING OPTICAL FIBER

(75) Inventors: Kazutoshi Kiuchi, Aichi (JP); Masayuki Uchida, Aichi (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/528,335

(22) Filed: Mar. 17, 2000

(30) Foreign Application Priority Data

Mar. 18, 1999 (JP) .......................... 11-074385

(51) Int. Cl.$^7$ ................................. A61B 5/00
(52) U.S. Cl. .................. 600/407; 600/476; 600/478; 250/458.1; 385/118
(58) Field of Search .................. 600/473, 476, 600/478, 407, 431, 433, 310, 312, 317, 182, 373, 544; 250/458.1, 459.1, 461.1, 461.2; 359/368; 385/118; 606/3, 10

(56) References Cited

U.S. PATENT DOCUMENTS

| | | | | | |
|---|---|---|---|---|---|
| 4,553,034 A | * | 11/1985 | Byers et al. | .............. | 250/458.1 |
| 5,111,821 A | * | 5/1992 | Potter | .......................... | 600/431 |
| 5,419,323 A | * | 5/1995 | Kittrell et al. | ............... | 600/476 |
| 5,916,171 A | * | 6/1999 | Mayevsky | .................. | 600/476 |
| 5,938,617 A | * | 8/1999 | Vo-Dinh | ..................... | 600/476 |
| 6,040,940 A | * | 3/2000 | Kawasaki | ................... | 359/389 |
| 6,066,123 A | * | 5/2000 | Li et al. | ....................... | 604/507 |
| 6,088,612 A | * | 7/2000 | Blair | .......................... | 600/407 |
| 6,201,989 B1 | * | 3/2001 | Whitehead | .................. | 600/476 |
| 6,289,229 B1 | * | 9/2001 | Crowley | ..................... | 600/310 |
| 6,293,911 B1 | * | 9/2001 | Imaizumi et al. | ........... | 600/160 |
| 6,327,410 B1 | * | 12/2001 | Walt et al. | .................. | 385/115 |

FOREIGN PATENT DOCUMENTS

JP          3-120446          5/1991

OTHER PUBLICATIONS

Patent Abstracts of Japan, English translation of abstract, "Fluorescence Measuring Instrument", Publication No. 03120446A, Date of Publication May 22, 1991, one page.

* cited by examiner

Primary Examiner—Shawna J Shaw
(74) Attorney, Agent, or Firm—Rosenthal & Osha L.L.P.

(57) ABSTRACT

The present invention provides an apparatus and a method for finding out a specific portion for recording the activity accurately and easily in recording the activity of an organism specimen in vivo. An organism specimen (3) with a fluorescent substance expressed at the specific portion (3a) is prepared. An optical fiber (7) is inserted into the organism specimen (3). An excitation rays (4) irradiate the inside of the organism specimen (3) through the optical fiber (7) by a first optical system (9) of a fluorescence microscope (6). The fluorescence (5) by the excitation rays (4) is observed through the optical fiber (7) by a second optical system (10) of the fluorescence microscope (6). In this case, the optical fiber (7) is inserted at the specific portion (3a) of the organism specimen or in the vicinity thereof. Since the fluorescence from the specific portion (3a) is guided to the fluorescence microscope through the optical fiber (7) so as to be incident on an eyepiece (16) of the second optical system (10), only by examining whether or not the fluorescence (5) is observed through the optical fiber (7) can the specific portion (3a) be judged.

4 Claims, 3 Drawing Sheets

METHOD FOR DETECTING A SPECIFIC PORTION OF ORGANISM SPECIMEN, METHOD FOR PHYSIOLOGICAL MEASUREMENT OF ORGANISM SPECIMEN, APPARATUS FOR DETECTING A SPECIFIC PORTION OF ORGANISM SPECIMEN, AND A DEVICE FOR HOLDING OPTICAL FIBER

BACKGROUND OF THE INVENTION

1. Field of the Invention

The present invention relates to a technique for monitoring and recording the activity of organism tissue in vivo, that is, keeping an organism specimen alive and monitoring a physiological change, in particular, it relates to a technique for enabling researchers to efficiently detect a specific portion to be the subject of interest in an organism specimen.

2. Description of the Prior Art

As a method for recording the activity of organism specimen, which receives a stimulus from the out side, that is, as a method for monitoring the change in physiological functions of organism tissue in vivo, an electrophysiological technique is conventionally used to extracellularly measure the action potential of nerve cells in the vicinity of a probe such as a tungsten electrode, the tip of which is inserted into a specific portion of organism specimen.

However, in case of recording the activity of organism tissue in vivo, since the portion wherein an observation subject such as the nerve cell exists can be roughly detected, a troublesome operation, which needs preparation of tissue slices as histochemical specimens to ascertain whether or not the monitoring area inserted with the probe is correct, is required after recording the activity and collecting the resultant data. For example, using a mouse as a specimen for recording the action potential of nerve cells at a specific portion of the brain in vivo, the following sequential operation is executed, roughly detecting a target portion according to the map information of mouse brain empirically obtained, inserting an electrode into the portion to record the action potential of nerve cells, taking out the brain to prepare section specimens for histochemistry, and estimating the electrophysiological data obtained and the portion of the brain defined.

As mentioned above, in case of conventional recordings of the activity at a specific portion of organism specimen in vivo, since the portion can be roughly detected, the section specimens of organism tissue are required to confirm the recorded portion to be correct after collecting electrophysiological data of interest. Therefore, if the recorded portion is not a desirable one, the above-mentioned operation should be repeated until the acquired result is a satisfactory one.

SUMMARY OF THE INVENTION

Accordingly, an object of the present invention is to provide an apparatus for detecting a specific portion and recording the activity of cells in an organism specimen in vivo, a method capable of finding the specific portion easily and a method capable of recording physiological activities in the specific portion accurately.

In order to solve problems mentioned above, the first aspect of the present invention is a method for detecting the specific portion, which comprised of the following steps; expressing a fluorescent substance (such as GFP: green fluorescent protein) at the specific portion of organism specimen, inserting an optical fiber into the organism specimen in vivo, performing irradiation with exciting rays through an optical fiber, and monitoring to detect the specific portion emitting the resultant fluorescence through the optical fiber.

According to the method for detecting the specific portion of organism specimen, an insertion of optical fiber into the specimen makes it easy to find a target portion by examining whether or not the fluorescence can be seen through the optical fiber.

The second aspect of the present invention is a method for monitoring the fluorescence from the specific portion with the fluorescent substance excited by the exciting rays through the optical fiber using a fluorescence microscope while irradiating the exciting rays from the fluorescence microscope to the inside of the organism specimen through the optical fiber.

According to the method for detecting the specific portion, since a spell of operation irradiating the inside of organism specimen with exciting rays and monitoring the fluorescence from the special portion excited by exciting rays through the optical fiber can be efficiently executed by use of a fluorescence microscope, the specific portion of organism specimen can be unearthed easier compared with the case of the first aspect.

Furthermore, the third aspect of the present invention is a method of physiological measurement comprised of the following steps; expressing a fluorescent substance at the specific portion of organism specimen, inserting an optical fiber into the specimen, performing irradiation of exciting rays to the inside of organism specimen through the optical fiber, monitoring the fluorescence from the specific portion excited by the exciting rays through the optical fiber, inserting a probe into the specific portion or in the vicinity thereof, and recording physiological activities at the specific portion or in the vicinity thereof via the probe.

According to the method of physiological measurement, since the specific portion of organism specimen can be easily unearthed only by inserting the optical fiber and examining whether or not the fluorescence can be seen through the optical fiber, the activity of organism specimen in vivo can be easily recorded by inserting the probe into the specific portion or in the vicinity thereof.

Moreover, the fourth aspect of the present invention is a method of physiological measurement according to the third aspect, wherein the specific portion is unearthed by monitoring the fluorescence from the specific portion excited by the exciting rays through the optical fiber using a fluorescence microscope while by irradiating exciting rays to the inside of organism specimen through the optical fiber using the fluorescence microscope, and the activity of the specific portion or in the vicinity thereof is measured by inserting the probe into the specific portion unearthed or in the vicinity thereof.

According to the method of physiological measurement, since both irradiation of exciting rays to the inside of organism specimen and monitoring of fluorescence excited by the exciting rays through the optical fiber can be efficiently executed by use of a fluorescence microscope, so that the specific portion of organism specimen can be further easily found out, an experiment for recording the activity of organism specimen in vivo can be executed easier compared with the case of the third aspect of inserting the probe into the specific portion or in the vicinity thereof for measurement.

Furthermore, the fifth aspect of the present invention is an apparatus comprised of an optical fiber which is inserted into an organism specimen, that is, the first optical system for irradiation of exciting rays to the inside of organism specimen through the optical fiber and the second optical system for monitoring of fluorescence excited by the exciting rays through the optical fiber.

According to the specific portion detecting apparatus, by inserting the optical fiber into the organism specimen with an fluorescent substance expressed at the specific portion for recording the activity, irradiating the exciting rays to the inside of the organism specimen through the optical fiber by the first optical system, and observing the fluorescence excited by the exciting rays through the optical fiber by the second optical system, the specific portion of the organism specimen can be easily found out. That is, by using the specific portion detecting apparatus according to the fifth aspect, a specific portion of an organism specimen can be easily found out by the specific portion detecting method according to the first aspect. Therefore, by inserting a probe into the found out specific portion or in the vicinity thereof for measurement, the activity recording experiment of the organism specimen in vivo can be easily executed.

Moreover, a sixth aspect of the present invention is a specific portion detecting apparatus comprising a fluorescence microscope for irradiating the exciting rays to an organism specimen through an objective lens and catching the fluorescence excited by the exciting rays by the objective, an optical fiber with one end to be inserted into the organism specimen, and an optical fiber holding device for holding the other end surface of the optical fiber, facing to the objective.

According to the specific portion detecting apparatus, since the operation of irradiating the exciting rays to the inside of the organism specimen through the optical fiber and observing the fluorescence excited by the exciting rays through the optical fiber can be efficiently executed using the fluorescence microscope, the specific portion of the organism specimen can be easily found out. That is, using the specific portion detecting apparatus according to the sixth aspect, a specific portion of an organism specimen can be easily found out by the specific portion detecting method according to the second aspect. Therefore, by inserting a probe into the specific portion found out or in the vicinity thereof for measurement, the activity recording experiment of the organism specimen in vivo can be easily executed.

Furthermore, the seventh aspect of the present invention is the specific portion detecting apparatus according to the sixth aspect, wherein the optical fiber holding device is fixed detachably on a stage of the fluorescence microscope. The stage herein denotes a placing base provided below the objective of the fluorescence microscope for placing a sample, movably in the horizontal direction and further in the vertical direction.

The specific portion detecting apparatus can be used as the specific portion detecting apparatus according to the sixth aspect with the optical fiber holding device fixed to the stage of the fluorescence microscope so as to hold the optical fiber, and it can be used as an ordinary fluorescence microscope with the optical fiber holding device detached from the stage of the fluorescence microscope.

Moreover, the eighth aspect of the present invention is the specific portion detecting apparatus according to the seventh aspect, wherein the optical fiber holding device comprises a flat plate-like pedestal fixed detachably to the stage of the fluorescence microscope, and a gripping device fixed to the pedestal for holding the end portion of the optical fiber perpendicular to the stage.

The specific portion detecting apparatus can be used as the specific portion detecting apparatus according to the sixth aspect with the pedestal of the optical fiber holding device fixed to the stage of fluorescence microscope so as to hold the optical fiber by the gripping device, and it can be used as an ordinary fluorescence microscope with the optical fiber holding device detached from the stage of fluorescence microscope.

Furthermore, the ninth aspect of the present invention is an optical fiber holding device comprising a flat plate-like pedestal fixed detachably to the stage of the fluorescence microscope, and a gripping device fixed to the pedestal for holding the end portion of the optical fiber perpendicular to the stage.

According to the optical fiber holding device, since it can be used as the specific portion detecting apparatus according to the sixth aspect with the pedestal fixed to the fluorescence microscope and the optical fiber held by the gripping device, a specific portion of an organism specimen can be easily found out using the fluorescence microscope.

As the pedestal in the eighth and ninth aspects, the plate having a size and shape fixed by a sample applanator provided on the stage, such as a glass plate used as a slide glass or a preparation, or a metal plate or a synthetic resin plate having the same size as the preparation can be preferably used.

DETAILED DESCRIPTION OF THE PREFERRED EMBODIMENTS

Hereinafter embodiments of the present invention will be explained with reference to the drawings.

Figure 1:
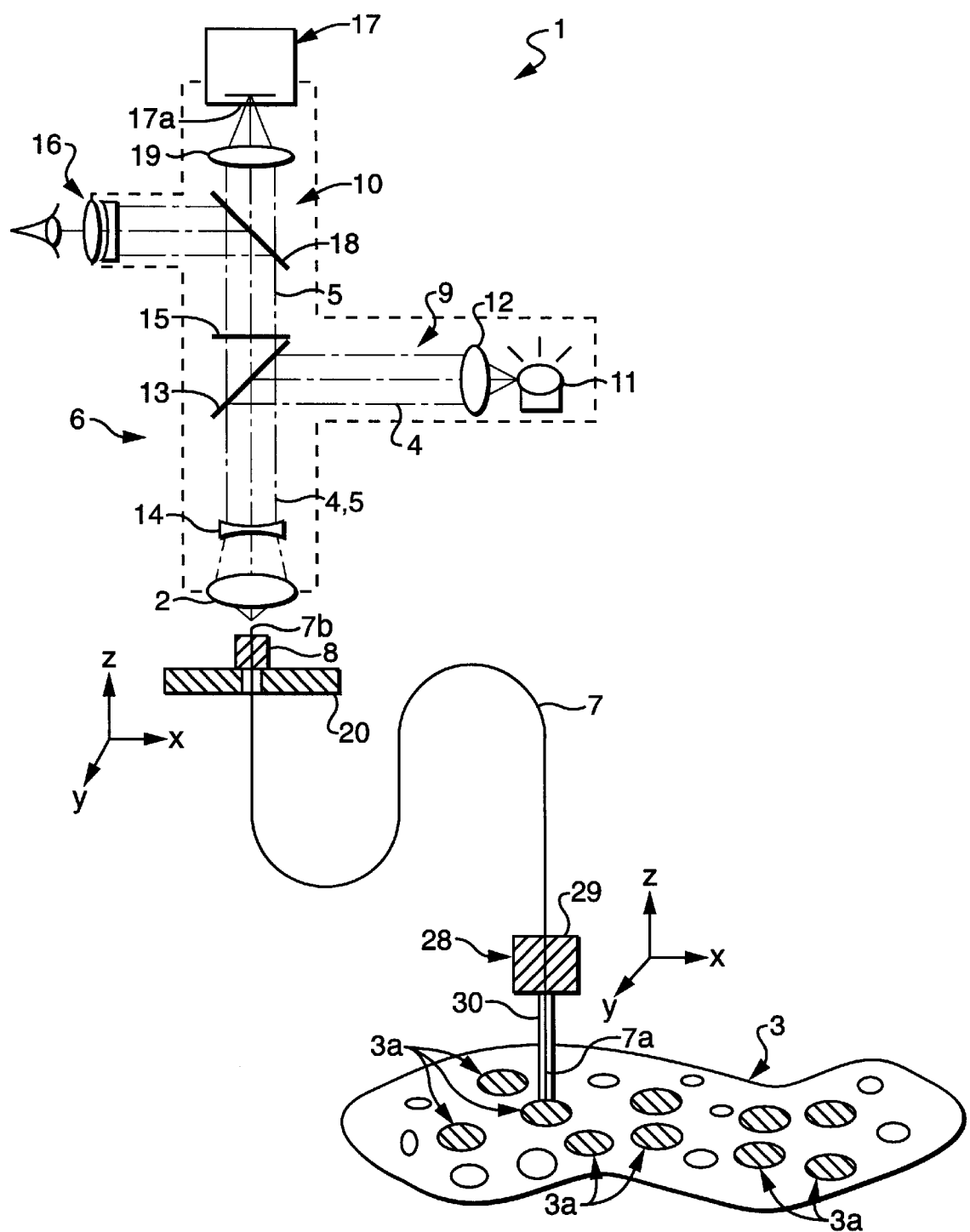
FIG. 1 is a schematic configuration diagram of a specific portion detecting apparatus according to an embodiment of the present invention.

FIG. 1 is a schematic configuration diagram of a specific portion detecting apparatus according to an embodiment of the present invention. The specific portion detecting apparatus 1 comprises a fluorescence microscope 6 for catching the fluorescence 5 excited by the exciting rays 4 from the objective while irradiating the exciting rays 4 to an organism specimen 3 through an objective 2 having a high numerical aperture n (such as n=0.7), an optical fiber 7 for inserting one end portion 7a into the organism specimen 3, and an optical fiber holding apparatus 8 for holding the optical fiber 7 with the other end surface 7b facing to the objective 2.

The fluorescence microscope 6 comprises the first optical system 9 for irradiating the exciting rays 4 into the organism specimen 3 through the optical fiber 7, and the second optical system 10 for observing the discharged fluorescence 5 excited by the exciting rays 4 through the optical fiber 7.

The first optical system 9 comprises an exciting rays source 11, a relay lens 12 for collecting and collimating the exciting rays 4 emitted from the exciting rays source 11, a dichroic mirror 13 for reflecting the exciting rays 4 from the relay lens 12 so as to be guided toward the objective 2 side, and a relay lens 14 for relaying the exciting rays 4 from the dichroic mirror 13 so as to be incident on substantially the entirety of the objective 2. The exciting rays source 11 generates the exciting rays 4 having a specific wavelength for exciting a fluorescent substance (such as GFP) specifically expressed in the organism specimen 3 by coloring or by the gene recombination technique. As the exciting rays source 11, a lamp or a laser light source is used. The dichroic mirror 13 has a characteristic of reflecting only the exciting rays 4 and transmitting rays of the other wavelength components.

The second optical system 10 comprises the relay lens 14 for collecting and collimating rays from the objective 2, the dichroic mirror 13 for transmitting rays from the relay lens 14, a filter 15 for transmitting only the fluorescence 5 emitted from the organism specimen 3 among the transmitted rays from the dichroic mirror 13 and absorbing rays of the other wavelength domain, and a half mirror 18 for splitting the transmitted rays from the filter 15 (fluorescence 5) into two directions, that is, to the eyepiece 16 side and the image pick-up device 17 side. In this embodiment, the transmitted rays from the filter 15 is reflected partially by the half mirror 18 so as to be incident on the eyepiece 16. In contrast, the rays transmitting the half mirror 18 is collected by a relay lens 19 so as to be focused on the rays received by the surface 17a of image pick-up device 17 such as a CCD.

Figure 2:
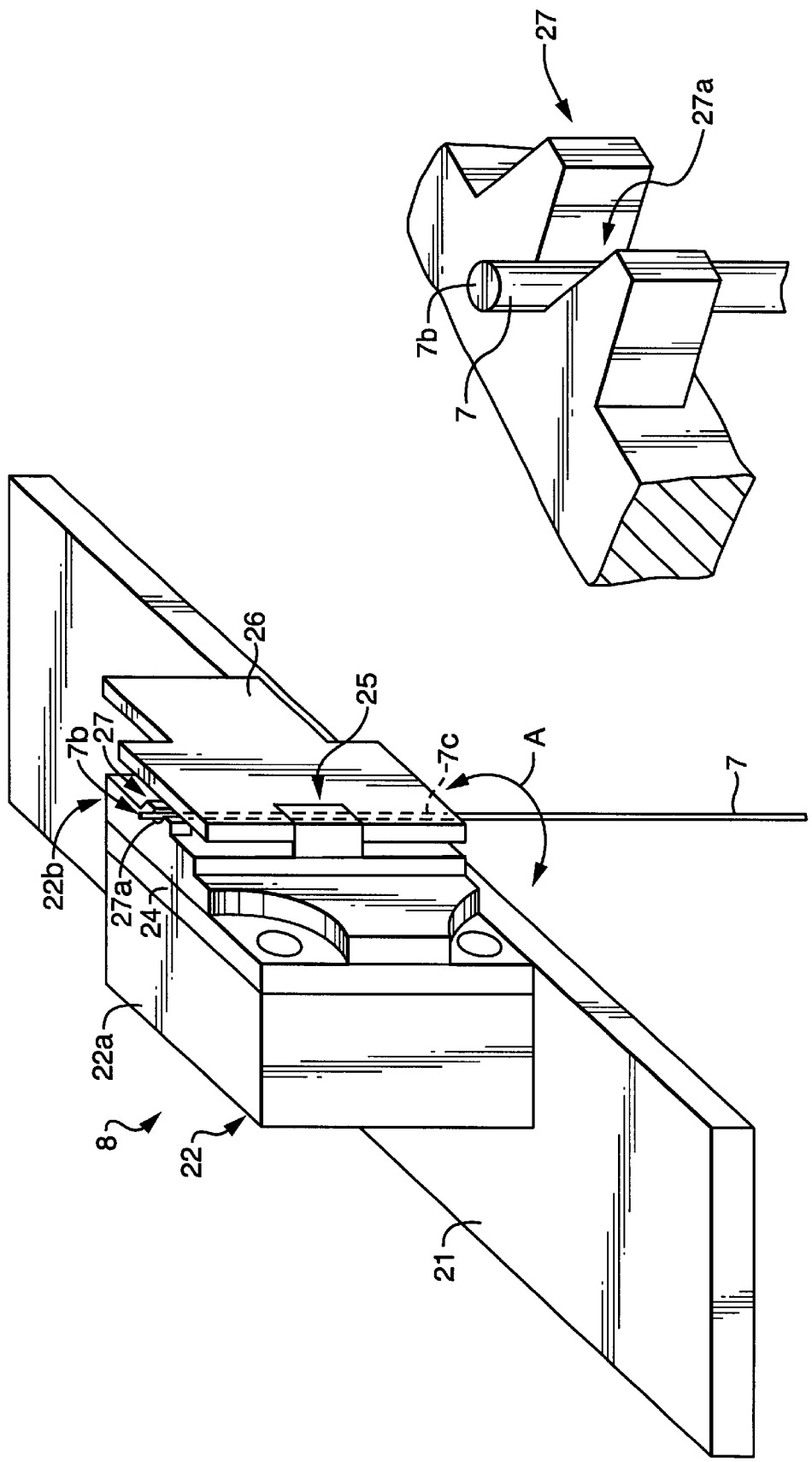
FIG. 2A is an enlarged perspective view of an optical fiber holding device shown in FIG. 1.
FIG. 2B is an enlarged view of the principal portion of FIG. 2A.

The optical fiber holding device 8 is fixed on the stage 20 of the fluorescence microscope 6. As shown in FIG. 2A, the optical fiber holding device 8 comprises a pedestal of rectangular flat plate 21, and a gripping device 22 for holding the end portion of the optical fiber 7. As the pedestal 21, a metal plate or a synthetic resin plate having the same size as a commercially available preparation can be used. The gripping device 22 is fixed to the center part of the upper surface of the pedestal 21 by bonding or screwing.

The gripping device 22 comprises a metal or synthetic resin main body 22a with a cube structure, and a gripping mechanism 23b provided on one side surface of the main body 22a. The gripping mechanism 23b comprises a substrate member 24 fixed to the main body 22a by bonding or by screwing, and a gripping plate 26 interlocked with the substrate member 24 rotatably in the longitudinal direction of the pedestal 21 (direction shown by the arrow A) via a hinge part 25.

As shown in FIGS. 2A and 2B, supporting parts 27 having a recess part 27a for receiving the optical fiber 7 are provided, projecting from the upper and lower end portions on one side of the substrate member 24 of the gripping mechanism 23b (in the state shown in FIG. 2A, the lower supporting part 27 is covered by the gripping plate 26). If the gripping plate 26 is rotated to the supporting part 27 side to its limit in the state that the end part (end part opposite to the side for inserting into the organism specimen 3) 7c of the optical fiber 7 engaged with the recess 27a of the upper and lower supporting part 27, the optical fiber 7 is held and fixed between the gripping plate 26 and the substrate member 24. Furthermore, at the same time, a lock mechanism (not illustrate) functions so that the gripping plate 26 is fixed in the state of holding the optical fiber 7.

By placing the optical fiber holding device 8 on the stage 20 with the pedestal 21 downward, and fixing the pedestal 21 by a sample applanating member (which in general comprises an applanating member for applanating a preparation from above, and a screw for adjusting the applanating force) provided on the stage 20, it can be fixed on the stage 20. By fixing the optical fiber holding device 8 on the stage 20, the end part 7c of the optical fiber 7 can be held perpendicular to the stage 20. Therefore, at the same time, the end surface 7b of the optical fiber 7 is exposed upward.

The position of the stage 20 can be adjusted by moving in the front, back, right and left directions (x axis and y axis directions) and up and down directions (z axis direction) according to the operation of moving mechanism (not illustrated). Therefore, by moving the stage 20 for adjusting the position after mounting the optical fiber holding device 8 on the stage 20 for holding the optical fiber 7, the end surface 7b of the optical fiber 7 can be positioned immediately below the objective 2 for aligning the optical axes thereof. By adjusting the height of the stage 20 in the state, the focal point of the objective 2 can be provided on the end surface 7b of the optical fiber 7.

In contrast, the end part 7a of the optical fiber 7 to be inserted into the organism specimen 3 is held by the optical fiber moving mechanism 28. The optical fiber moving mechanism 28 comprises a moving member 29 to be moved exactly in the front, back, right and left directions (x axis and y axis directions) and in the up and down directions (z axis direction) with the end part 7a of the optical fiber 7 facing downward in the vertical direction held thereby, and a metal (for example, stainless steel) support tube 30 fixed to the lower part of moving member 29 for supporting the end part 7a of the optical fiber 7 at the time of inserting the end part 7a of the optical fiber 7 into the organism specimen 3.

According to the specific portion detecting apparatus 1 with the above-mentioned configuration, the specific portion 3a of the organism specimen 3 can be easily found out by preparing the organism specimen 3 with a fluorescent substance expressed at the specific portion 3a for recording the activity, inserting the optical fiber 7 into the organism specimen 3, irradiating the exciting rays 4 to the inside of the organism specimen 3 through the optical fiber 7 by the first optical system 9 of the fluorescence microscope 6, and observing the fluorescence 5 excited by the exciting rays 4 through the optical fiber 7 by the second optical system 10 of the fluorescence microscope 6. That is, in that case, the optical fiber 7 is inserted at the specific portion 3a of the organism specimen 3 or in the vicinity thereof, since the fluorescence from the specific portion 3a is guided to the fluorescence microscope 6 through the optical fiber 7 so as to be incident on the eyepiece 16 of the second optical system 10, only by examining whether or not the fluorescence 5 can be observed by looking into the eyepiece 16, whether or not the portion wherein the optical fiber 7 is inserted is the specific portion 3a can be judged. Moreover, since a weak fluorescence 5 can be detected in the amplified state by the image pick-up device 17 and displaying the data of the receiving light signal and the received image on a monitor, the specific portion 3a can be found out further certainly. Moreover, by moving the end part 7a of the optical fiber 7 to be inserted into the organism specimen 3 by the optical fiber moving mechanism 28, the inserting position of the optical fiber 7 can be changed minutely, and thus the fine specific portion 3a can be found out certainly.

Furthermore, according to the specific portion detecting apparatus 1, since the operation of irradiating the exciting rays 4 to the inside of the organism specimen 3 through the optical fiber 7 and observing the fluorescence 5 excited by the exciting rays 4 through the optical fiber 7 can be efficiently executed using the fluorescence microscope 6, which is an accustomed experiment device for a researcher in the physiological field, the operation of finding out the specific portion 3a can be executed extremely and efficiently.

As a result, the measurement of action potential in vivo by inserting a probe at the specific portion 3a of the organism specimen 3 or in the vicinity thereof can be executed accurately and easily.

Therefore, since the conventional troublesome operation of preparing a specimen section after recording the action potential by inserting a probe into the organism specimen, and collating the resultant records and the portion of the specimen section can be eliminated, drastic promotion of the study of the organism specimen in vivo can be expected. For example, the action of the brain tissue in vivo of a transgenic animal with a specific region of the brain tissue labeled by the GFP, such as a transgenic mouse with the GFP expressed at a specific nerve cell in the brain can be recorded much simpler than the conventional methods, and thus it can largely contribute to the elucidation of the brain function.

Moreover, since the specific portion detecting apparatus 1 can be used as an ordinary fluorescence microscope with the optical fiber holding device 8 detached from the stage 20 of the fluorescence microscope 6, it can be used according to the various observation subjects or applications.

Furthermore, since the optical fiber holding device 8 can be easily mounted on a fluorescence microscope widely used in this study field, the above-mentioned specific portion detecting apparatus 1 can be realized by mounting the optical fiber holding device 8 on a fluorescence microscope.

Although the apparatus configuration comprising both the eyepiece 16 and the image pick-up device 17 is explained in the above-mentioned embodiment, a configuration comprising only one of the eyepiece 16 and the image pick-up device 17 can be adopted as well.

Moreover, the optical fiber moving mechanism 28 need not be always provided, but the optical fiber 7 can be inserted into the organism specimen 3 by the manual operation.

Figure 3:
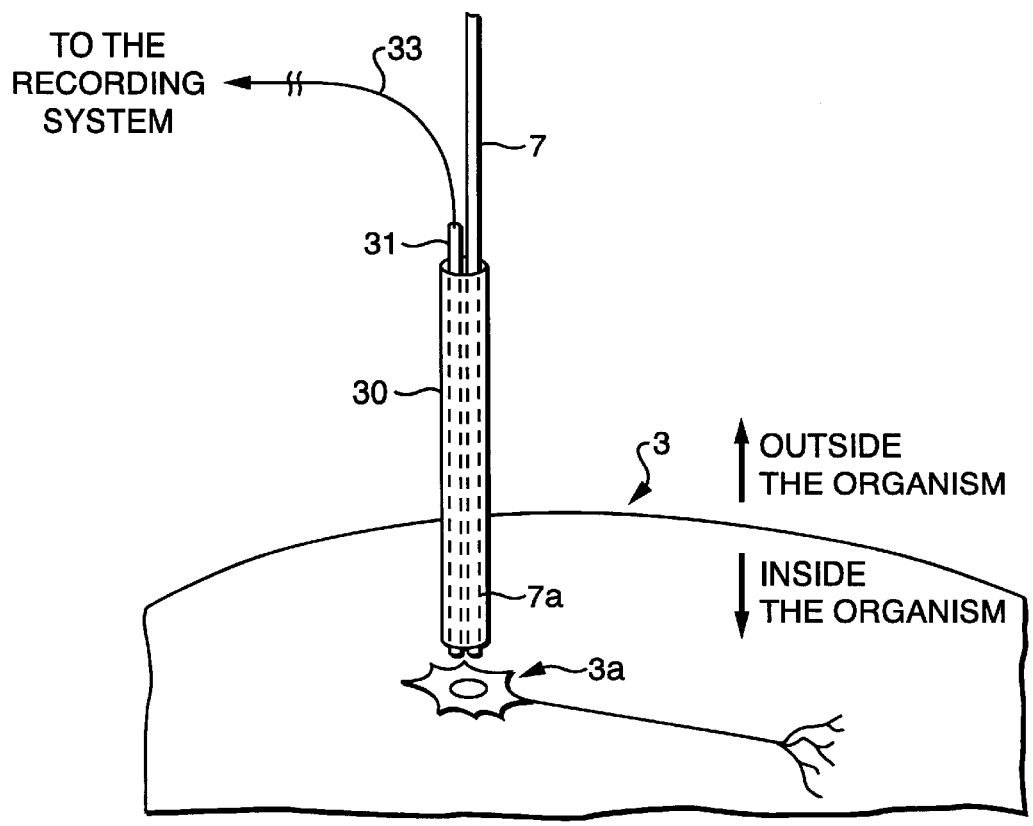
FIG. 3 is a schematic configuration diagram of the principal part of a specific portion detecting apparatus according to another embodiment of the present invention.
Figure 4:
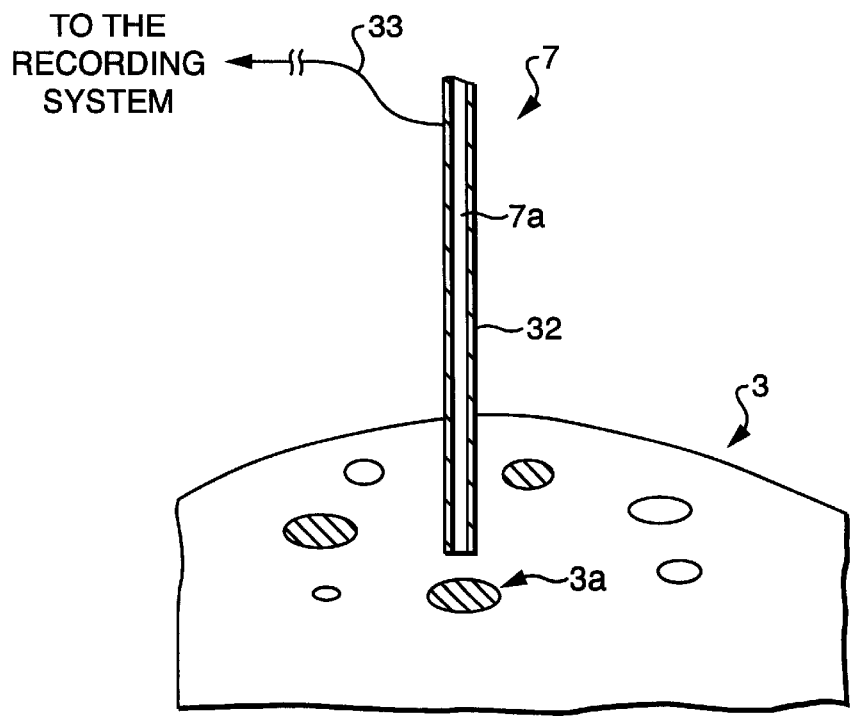
FIG. 4 is a schematic configuration diagram of the principal part of a specific portion detecting apparatus according to still another embodiment of the present invention.

Furthermore, as shown in FIG. 3, a probe 31 for detecting the action potential can be provided at the inserting side end part 7a of the optical fiber 7 so that the probe 31 is inserted into the organism specimen 3 with the optical fiber 7. Moreover, as shown in FIG. 4, the outer peripheral surface of the inserting side end part 7a of the optical fiber 7 coated with a probe electrode layer 32 can be inserted into the organism specimen 3. The probe 31 and the probe electrode layer 31 are connected with the recording system via a signal line 33. In case of the configuration of FIG. 4, since detection of the specific portion 3a and measurement of the action potential can be executed simultaneously as well as the strength of the optical fiber 7 can be reinforced by the probe electrode layer 32, deformation of the optical fiber 7 can be prevented. Therefore, detection of the specific portion 3a and measurement of the action potential can be executed extremely, efficiently and accurately.

As heretofore explained, the present invention provides the following advantages.

According to the specific portion detecting method of the first aspect, in recording the activity of an organism specimen in vivo, the specific portion of the organism specimen for recording the activity can be found out easily only by inserting an optical fiber into the organism specimen and examining whether or not the fluorescence can be observed through the optical fiber.

Moreover, according to the specific portion detecting method of the second aspect, since the operation of irradiating the exciting rays to the inside of the organism specimen through the optical fiber and observing the fluorescence excited by the exciting rays through the optical fiber can be executed efficiently by using the fluorescence microscope, the specific portion for recording the activity of the organism specimen can be found out easier compared with the case of the first aspect.

Furthermore, according to the physiological measuring method of the third aspect, since the specific portion of the organism specimen for recording the activity can be found out easily only by inserting an optical fiber into the organism specimen and examining whether or not the fluorescence can be observed through the optical fiber, the operation recording the activity of the organism specimen in vivo can be executed easily by inserting the probe at the specific portion or in the vicinity thereof for measurement.

Moreover, according to the physiological measuring method of the fourth aspect, since the operation of irradiating the exciting rays to the inside of the organism specimen through the optical fiber and observing the fluorescence excited by the exciting rays through the optical fiber can be efficiently executed using the fluorescence microscope so that the specific portion of the organism specimen can be found out further easily, the activity recording operation of the organism specimen in vivo can be executed easier than the case of the third aspect by inserting the probe at the specific portion or in the vicinity thereof for measurement.

Furthermore, according to the specific portion detecting apparatus of the fifth aspect, in recording the activity of the organism specimen in vivo, by inserting the optical fiber into the organism specimen, and observing the fluorescence excited by the exciting rays through the optical fiber, the specific portion for recording the activity of the organism specimen can be easily found out.

Moreover, according to the specific portion detecting apparatus of the sixth aspect, since the operation of irradiating the exciting rays to the inside of the organism specimen through the optical fiber and observing the fluorescence excited by the exciting rays through the optical fiber can be executed efficiently by using the fluorescence microscope, the specific portion for recording the activity of the organism specimen can be found out easier compared with the case of the apparatus according to the fifth aspect.

Furthermore, according to the specific portion detecting apparatus of the seventh aspect, if the optical fiber holding device is fixed to the stage of fluorescence microscope so as to hold the optical fiber, it can be used as the specific portion detecting apparatus according to the sixth aspect, and if the optical fiber holding device is detached from the stage of fluorescence microscope, it can be used as an ordinary fluorescence microscope, and thus it can be used according to the various observation subjects or applications.

Moreover, according to the specific portion detecting apparatus of the eighth aspect, if the pedestal of the optical fiber holding device is fixed to the stage of fluorescence microscope so as to hold the optical fiber by the gripping device, it can be used as the specific portion detecting apparatus according to the sixth aspect, and if the optical fiber holding device is detached from the stage of fluorescence microscope, it can be used as an ordinary fluorescence microscope, and thus it can be used according to the various observation subjects or applications.

Furthermore, according to the optical fiber holding device of the ninth aspect, if the pedestal is conventionally fixed to the fluorescence microscope and the optical fiber is held by the gripping device, it can be used as the specific portion detecting apparatus according to the sixth aspect, and thus a specific portion of an organism specimen can be found out easily by using a fluorescence microscope.

What is claimed is:

1. A method for detecting a specific portion of an organism specimen and measuring physiological activity thereof in vivo, comprising:

expressing a fluorescent substance at the specific portion of the organism specimen;

inserting one end of an optical fiber into a position of the organism specimen, the insertion end of the optical fiber attached to a probe connected to a recording system via a signal line and the opposite end of the optical fiber connected to a fluorescence microscope;

irradiating excitation rays to the organism specimen from the fluorescence microscope through the optical fiber at the position where the optical fiber is inserted, and examining the organism specimen at the position by using the fluorescence microscope;

measuring a physiological activity of the specific portion of the organism specimen by using the probe and the recording system if fluorescence is observed at the position of the organism specimen; and shifting the optical fiber and probe to another position of the organism specimen to examine the organism specimen at the another position if fluorescence is not observed, and repeating this procedure until fluorescence is observed by the fluorescence microscope.

2. An apparatus for detecting a specific portion of an organism specimen and measuring physiological activity thereof in vivo, comprising:

a fluorescence microscope for irradiating excitation rays to the organism specimen expressing a fluorescent substance and observing fluorescence excited by the excitation rays;

an optical fiber for transmitting the excitation rays and observing fluorescence therethrough, a first end of the optical fiber connected to the fluorescence microscope and a second end of the optical fiber adapted to be inserted into the organism specimen;

a probe for measuring physiological activity of the organism specimen, the probe connected to a recording system via a signal line, and the probe attached to the second end of the optical fiber; and an optical fiber moving mechanism for holding and shifting the optical fiber, the mechanism configured to shift the second end of the optical fiber from one position of the organism specimen to another position thereof to enable an operator to detect the specific portion of the organism specimen where the fluorescent substance is expressed by determining whether fluorescence is observed through the optical fiber.

3. A method for detecting a specific portion of an organism specimen and measuring physiological activity thereof in vivo, comprising:

expressing a fluorescent substance at the specific portion of the organism specimen;

inserting one end of an optical fiber into a position of the organism specimen, the insertion end of the optical fiber coated with a probe electrode layer that is connected to a recording system via a signal line, the opposite end of the optical fiber connected to a fluorescence microscope;

irradiating excitation rays to the organism specimen from the fluorescence microscope through the optical fiber at the position where the optical fiber is inserted, and examining the organism specimen at the position by using the fluorescence microscope;

measuring a physiological activity of the specific portion of the organism specimen by using the probe electrode layer and the recording system if fluorescence is observed at the position of the organism specimen; and shifting the insertion end of the optical fiber to another position of the organism specimen to examine the organism specimen at the another position if fluorescence is not observed, and repeating this procedure until fluorescence is observed by the fluorescence microscope.

4. An apparatus for detecting a specific portion of an organism specimen and measuring physiological activity thereof in vivo, comprising:

a fluorescence microscope for irradiating excitation rays to the organism specimen expressing a fluorescent substance and observing fluorescence excited by the excitation rays;

an optical fiber adapted to be inserted at one end thereof into the organism specimen for transmitting the excitation rays and observing fluorescence therethrough, the opposite end of the optical fiber connected to the fluorescence microscope and the insertion end of the optical fiber coated with a probe electrode layer for measuring physiological activity of the organism specimen and connected via a signal line to a recording system; and an optical fiber moving mechanism for holding and shifting the optical fiber, the mechanism configured to shift the insertion end of the optical fiber from one position of the organism specimen to another position thereof to enable an operator to detect the specific portion of the organism specimen where the fluorescent substance is expressed by determining whether fluorescence is observed through the optical fiber.

* * * * *

UNITED STATES PATENT AND TRADEMARK OFFICE
CERTIFICATE OF CORRECTION

PATENT NO. : 6,600,943 B1
DATED : July 29, 2003
INVENTOR(S) : Kazutoshi Kiuchi et al.

It is certified that error appears in the above-identified patent and that said Letters Patent is hereby corrected as shown below:

<u>Title page, Item [54], and Column 1, line 1</u>
Please replace with -- METHODS AND APPARATUS FOR DETECTING A SPECIFIC PORTION OF AN ORGANISM SPECIMEN AND PHYSIOLOGICAL MEASUREMENT THEREOF --.

Signed and Sealed this

Thirteenth Day of July, 2004

JON W. DUDAS
*Acting Director of the United States Patent and Trademark Office*